United States Patent
Burton et al.

(10) Patent No.: US 7,395,822 B1
(45) Date of Patent: Jul. 8, 2008

(54) METHOD AND APPARATUS FOR ADJUSTABLE SLING FOR TREATMENT OF URINARY STRESS INCONTINENCE

(75) Inventors: John H. Burton, Minnetonka, MN (US); Timothy C. Cook, Wayzata, MN (US)

(73) Assignee: Uromedica, Inc., Plymouth, MN (US)

( * ) Notice: Subject to any disclaimer, the term of this patent is extended or adjusted under 35 U.S.C. 154(b) by 0 days.

(21) Appl. No.: 09/561,551

(22) Filed: Apr. 28, 2000

(51) Int. Cl.
 *A61F 5/48* (2006.01)
(52) U.S. Cl. .......................... 128/885; 600/29
(58) Field of Classification Search ............. 128/885, 128/886, DIG. 25; 600/29–31
See application file for complete search history.

(56) References Cited

U.S. PATENT DOCUMENTS

| | | | |
|---|---|---|---|
| 3,138,161 A | 6/1964 | Allen | |
| 4,019,499 A | 4/1977 | Fitzgerald | 128/1 R |
| 4,553,959 A | 11/1985 | Hickey et al. | 604/96 |
| 4,559,043 A | 12/1985 | Whitehouse et al. | 604/201 |
| 4,669,478 A | 6/1987 | Robertson | 128/630 |
| 4,686,962 A | 8/1987 | Haber | 128/1 R |
| 4,773,393 A | 9/1988 | Haber et al. | 600/30 |
| 4,784,660 A | 11/1988 | Fischell | 623/14 |
| 4,802,479 A | 2/1989 | Haber et al. | 128/344 |
| 4,817,637 A | 4/1989 | Hillegass et al. | 128/899 |
| 4,832,680 A | 5/1989 | Haber et al. | 600/31 |
| 4,846,784 A | 7/1989 | Haber | 600/29 |
| 4,857,041 A * | 8/1989 | Annis | 600/30 |
| 4,909,785 A | 3/1990 | Burton et al. | 604/54 |
| 4,938,760 A | 7/1990 | Burton et al. | 600/29 |
| 4,969,474 A | 11/1990 | Schwarz | 128/885 |
| 4,969,892 A | 11/1990 | Burton et al. | 606/218 |
| 5,012,822 A | 5/1991 | Schwarz | 128/885 |
| 5,041,136 A * | 8/1991 | Wascher | 600/30 |
| 5,047,055 A | 9/1991 | Bao et al. | 623/17 |
| 5,064,434 A | 11/1991 | Haber | 623/11 |
| 5,097,848 A | 3/1992 | Schwarz | 128/885 |
| 5,112,303 A | 5/1992 | Pudenz et al. | 604/49 |
| 5,123,428 A | 6/1992 | Schwarz | 128/885 |

(Continued)

FOREIGN PATENT DOCUMENTS

CA 2022709 2/1991

(Continued)

OTHER PUBLICATIONS

U.S. Appl. No. 09/477,977, Burton J. et al.

(Continued)

*Primary Examiner*—Michael A. Brown
(74) *Attorney, Agent, or Firm*—Schwegman, Lundberg & Woessner, P.A.

(57) ABSTRACT

An method and apparatus for an adjustable sling for treatment of urinary stress incontinence. The present system includes apparatus and methods for postoperative adjustment of sling tension using adjustable elements in the sling assembly. The present system also provides a number of demonstrative embodiments for an adjustable sling where positioning of the bladder is controlled using the adjustable sling and where coaptation of the urethra is controlled by postoperative inflation of one or more balloons mounted in a sling cup.

Methods and apparatus are provided for adjusting the adjustable sling after surgical implantation. In one embodiment a self sealing septum is located near the skin for convenient filling using a syringe. Multiple port embodiments are also discussed.

27 Claims, 10 Drawing Sheets

U.S. PATENT DOCUMENTS

| | | | |
|---|---|---|---|
| 5,133,753 A | 7/1992 | Bark et al. | 623/7 |
| 5,149,052 A | 9/1992 | Stoy et al. | 249/105 |
| 5,154,187 A | 10/1992 | Brownlee | 128/888 |
| 5,181,921 A | 1/1993 | Makita et al. | 606/195 |
| 5,192,326 A | 3/1993 | Bao et al. | 623/17 |
| 5,304,123 A | 4/1994 | Atala et al. | 604/54 |
| 5,334,153 A | 8/1994 | McIntyre et al. | 604/99 |
| 5,336,263 A | 8/1994 | Ersek et al. | 623/11 |
| 5,376,117 A | 12/1994 | Pinchuk et al. | 623/8 |
| 5,383,896 A | 1/1995 | Gershony et al. | 606/213 |
| 5,385,561 A | 1/1995 | Cerny | 604/264 |
| 5,411,475 A | 5/1995 | Atala et al. | 604/54 |
| 5,437,603 A | 8/1995 | Cerny et al. | 600/29 |
| 5,451,406 A | 9/1995 | Lawin et al. | 424/423 |
| 5,480,430 A | 1/1996 | Carlisle et al. | 623/8 |
| 5,483,976 A | 1/1996 | McLaughlin et al. | 128/885 |
| 5,496,370 A | 3/1996 | Hamas | 623/11 |
| 5,499,994 A | 3/1996 | Tihon et al. | 606/192 |
| 5,518,504 A | 5/1996 | Polyak | 623/14 |
| 5,520,700 A | 5/1996 | Beyar et al. | 606/139 |
| 5,534,023 A | 7/1996 | Henley | 623/8 |
| 5,547,472 A | 8/1996 | Onishi et al. | |
| 5,575,771 A | 11/1996 | Walinsky | 604/96 |
| 5,578,009 A | 11/1996 | Kraus et al. | 604/96 |
| 5,634,877 A | 6/1997 | Salama | 600/29 |
| 5,637,074 A | 6/1997 | Andino et al. | 600/29 |
| 5,647,836 A | 7/1997 | Blake, III et al. | 600/30 |
| 5,687,714 A | 11/1997 | Kolobow et al. | |
| 5,749,826 A | 5/1998 | Faulkner | 600/29 |
| 5,830,228 A | 11/1998 | Knapp et al. | 606/195 |
| 5,938,669 A * | 8/1999 | Klaiber | 600/31 |
| 5,964,806 A | 10/1999 | Cook et al. | 623/14 |
| 5,976,186 A | 11/1999 | Bao et al. | 623/17 |
| 6,005,020 A | 12/1999 | Loomis | 523/105 |
| 6,021,781 A | 2/2000 | Thompson et al. | 128/898 |
| 6,033,413 A | 3/2000 | Mikus et al. | 606/108 |
| 6,039,686 A | 3/2000 | Kovac | 600/30 |
| 6,042,536 A | 3/2000 | Tihon et al. | 600/37 |
| 6,045,498 A | 4/2000 | Burton et al. | 600/30 |
| 6,050,937 A | 4/2000 | Benderev | 600/37 |
| 6,053,935 A | 4/2000 | Brenneman et al. | 606/232 |
| 6,095,969 A | 8/2000 | Karram et al. | 600/31 |
| 6,099,547 A | 8/2000 | Gellman et al. | 606/198 |
| 6,110,101 A * | 8/2000 | Tihon et al. | 600/37 |
| 6,110,191 A | 8/2000 | Dehdashtian et al. | |
| 6,117,067 A * | 9/2000 | Gil-Vernet | 600/30 |
| 6,120,539 A | 9/2000 | Eldridge et al. | 623/11.11 |
| 6,132,465 A | 10/2000 | Ray et al. | 623/17.16 |
| 6,167,886 B1 | 1/2001 | Engel et al. | 128/885 |
| 6,171,231 B1 | 1/2001 | Connolly | 600/29 |
| 6,419,624 B1 | 7/2002 | Burton et al. | 600/29 |
| 6,419,701 B1 | 7/2002 | Cook et al. | 623/14.13 |
| 6,423,080 B1 | 7/2002 | Gellman et al. | |
| 6,579,224 B1 | 6/2003 | Burton et al. | 600/30 |
| 6,645,138 B2 | 11/2003 | Cook et al. | 600/30 |
| 6,752,814 B2 | 6/2004 | Gellman et al. | |
| 6,786,861 B1 | 9/2004 | Pretorius | |
| 7,014,606 B2 | 3/2006 | Burton et al. | |
| 2002/0055748 A1 | 5/2002 | Gellman et al. | |
| 2002/0156342 A1 | 10/2002 | Burton et al. | 600/29 |
| 2004/0015045 A1 | 1/2004 | Burton et al. | 600/30 |
| 2004/0230206 A1 | 11/2004 | Gellman et al. | |
| 2004/0230207 A1 | 11/2004 | Gellman et al. | |
| 2005/0027161 A1 | 2/2005 | Cook et al. | |
| 2006/0281964 A1 | 12/2006 | Burton et al. | |

FOREIGN PATENT DOCUMENTS

| | | |
|---|---|---|
| EP | 0639355 | 8/1993 |
| EP | 0784987 2 | 7/1997 |
| EP | 0941712 | 8/1998 |
| WO | WO-91/00069 | 1/1991 |
| WO | 96/01597 | 1/1996 |
| WO | WO-98/20812 | 5/1998 |
| WO | WO-9835632 A1 | 8/1998 |
| WO | WO-98/56311 | 12/1998 |
| WO | 00/18319 | 4/2000 |
| WO | WO-0066030 A1 | 11/2000 |

OTHER PUBLICATIONS

U.S. Appl. No. 10/673,028, filed May 5, 2003, Burton J, et al.

Lima, Salvador C., et al., "Combined Use of Enterocystoplasty and a new Type of Artificial Sphincter In The Treatment of Urinary Incontinence", *The Journal of Urology*, 156(2 Pt 2), (Applicant notes that the attached cover sheet states "Papers Presented at Annual Meeting of the Section on Urology, American Academy of Pediatrics", San Francisco, CA Oct. 14-16, 1995),(Aug. 1996),622-624.

Lima, S.V.C., "Further Experience with the Periurethral Expander: A New Type of Artificial Sphincter", *British Journal of Urology* (1997), 460-462.

* cited by examiner

METHOD AND APPARATUS FOR ADJUSTABLE SLING FOR TREATMENT OF URINARY STRESS INCONTINENCE

FIELD OF THE INVENTION

The present invention relates generally to treatment of urinary stress incontinence and in particular to a method and apparatus for treatment of stress urinary incontinence using an adjustable sling.

BACKGROUND

Urinary stress incontinence arises when an increase in abdominal pressure, such as from laughing, coughing, lifting, or exercise, results in urinary leakage. Normally, the urethra, which is the urinary lumen which passes urine from the bladder, will not leak with ordinary increases in abdominal pressure, also referred to as stress. However there are two conditions, referred to as type II and type III that commonly lead to incontinence.

Type II incontinence, also referred to as hypermobility, occurs when the support structures of the pelvic floor have been weakened, for instance from childbirth. This allows the bladder to descend below its normal location in the abdominal cavity and the bladder neck, where it joins the urethra, to funnel open under increased abdominal pressure.

Type II incontinence has most often been treated by a class of surgical procedures called suspensions of which there are many variations. Variations such as the Marshal-Marchetti-Krantz or the Burch procedures are quite invasive, requiring an abdominal incision. Other variations, generally called needle suspensions and including the Stamey and Raz procedures, are less invasive and may be done on an outpatient basis. Generally these procedures place sutures into tissue on either side of the urethra near the bladder neck and then lift or suspend the urethra and bladder from a higher anchoring point such the pubic bone, coopers ligament or the rectus abdominis muscle. This support compensates for weakness of the pelvic floor.

Unfortunately it has been found that these procedures, especially the needle suspensions, often fail over time because the sutures pull through the tissue on either side of the bladder neck or the tissue continues to sag between these points. Another concern is that if the bladder neck is lifted too high the patient may be put into urinary obstruction. Still another concern is that too much elevation may induce urge incontinence where the patient feels a need to urinate even when the bladder is not full. These later conditions may not be detected until after the surgery and the patient is up and around. In order to address some of these problems U.S. Pat. Nos. 4,938,760 and 4,969,892 propose a mechanism for allowing postoperative adjustment to the degree of suspension.

The other common cause of stress incontinence, type III also called intrinsic sphincter deficiency, occurs when the urinary sphincter which controls flow of urine from the bladder is dysfunctional. This may be caused by trauma, urethral scarring or any of a number of neurological conditions. For type III incontinence the most common treatment has been a class of surgical procedures called slings.

Generally a sling or strap of material is placed between the urethra and vagina and the ends are attached to the same selection of higher anchoring points as for a suspension procedure. Pressure of the sling on the underside of the urethra causes closing or coaptation of the urethra to compensate for the dysfunctional sphincter. Another way to achieve coaptation would be to provide an expandable element or elements such as balloons on the sling underneath or alongside the urethra. The sling may be made from artificial material such as polypropylene mesh, autologous tissue harvested from the patient such as rectus fascia, or cadaveric fascia latta.

While originally intended to provide coaptation for treating type III incontinence it has been recognized that slings also provide the support function sought by suspension procedures. While slings are somewhat more invasive than needle suspensions, they provide more reliable support since the sling is a continuous piece of material that goes underneath the urethra rather than being attached to fallible tissue alongside. At the same time it has also been recognized that mast stress incontinent patients do not have pure type II or type III but rather some of both. Often treating one of these conditions will unmask the presence of the other.

For these reasons surgeons are more and more turning to slings to treat both types of stress incontinence. Nevertheless slings are still prone to some of the same problems as suspensions. Often it is not possible to tell if there has been enough coaptation or suspension to provide continence without urinary obstruction before the patient has recovered. Another problematic disorder which may result from the foregoing procedures is called "postsurgical urgency," which is caused by improperly applied pressure to the periurethral tissues in which innervation is very dense causing hyperactivity of the bladder and urethra. This disorder causes the patient to feel an urgency to void when their bladder does not require voiding. Amelioration of the foregoing problems generally entails a second open surgical procedure to reduce the pressure on the bladder neck and proximal urethra. Thus, there is a need in the art for an improved sling for the treatment of urinary stress incontinence.

SUMMARY

The present invention provides a method and apparatus for an adjustable sling for treatment of urinary stress incontinence. The method and apparatus provide for sling adjustment peri-operatively and post-operatively for treatment of different urinary stress incontinence types and provide adjustable urethral positioning and adjustable urethral coaptation. The present system includes apparatus and methods for postoperative adjustment of sling tension using adjustable elements in the sling assembly. The present system also provides a number of demonstrative embodiments for an adjustable sling where positioning of the bladder is controlled using the adjustable sling and where coaptation of the urethra is controlled by postoperative inflation of one or more balloons mounted in a sling cup.

Methods and apparatus are provided for adjusting the adjustable sling after surgical implantation. In one embodiment a self sealing septum is located near the skin for convenient filling using a syringe. Multiple port embodiments are also discussed.

This summary is intended to be an overview of the subject matter of the present system and is not intended to be exhaustive or limiting. The invention is determined by the scope of the appended claims and their equivalents.

DETAILED DESCRIPTION

This detailed description provides a number of different embodiments methods and apparatus related to the present system. The embodiments provided herein are not intended in an exclusive or limited sense, and variations may exist in organization, dimension, chemical composition, and mechanical design and configuration, without departing from the claimed invention, the scope of which is provided by the appended claims and their equivalents.

Figure 1:
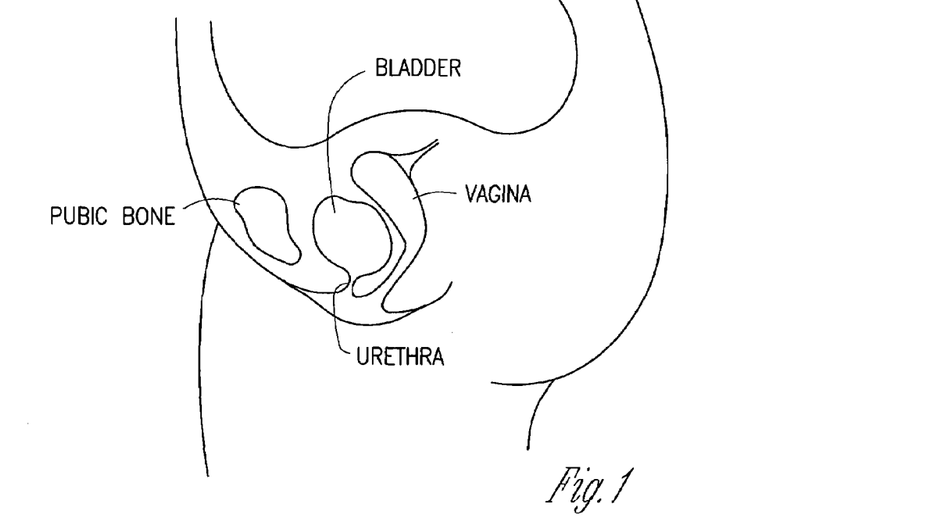
FIG. 1 is a side cross sectional drawing of a female anatomy showing the bladder, urethra, vagina, and pubic bone in a patient with pelvic floor dysfunction and loss of support giving rise to urethral hypermobility, thus resulting in the displacement of the bladder.

FIG. 1 is a side cross sectional drawing of a female anatomy showing the bladder, urethra, vagina, and pubic bone in a patient with pelvic floor dysfunction and loss of support giving rise to urethral hypermobility, thus resulting in the displacement of the bladder. When the patient is laughing, coughing, lifting, or exercising, the abdominal pressure is increased momentarily. For patients with type II stress incontinence, the result may be a shifting or "hypermobility" of the bladder near the region of the bladder neck, which results in unwanted urine leakage. This problem is reduced by adding lift and support to the area of the bladder near the bladder neck using a sling.

Figure 2:
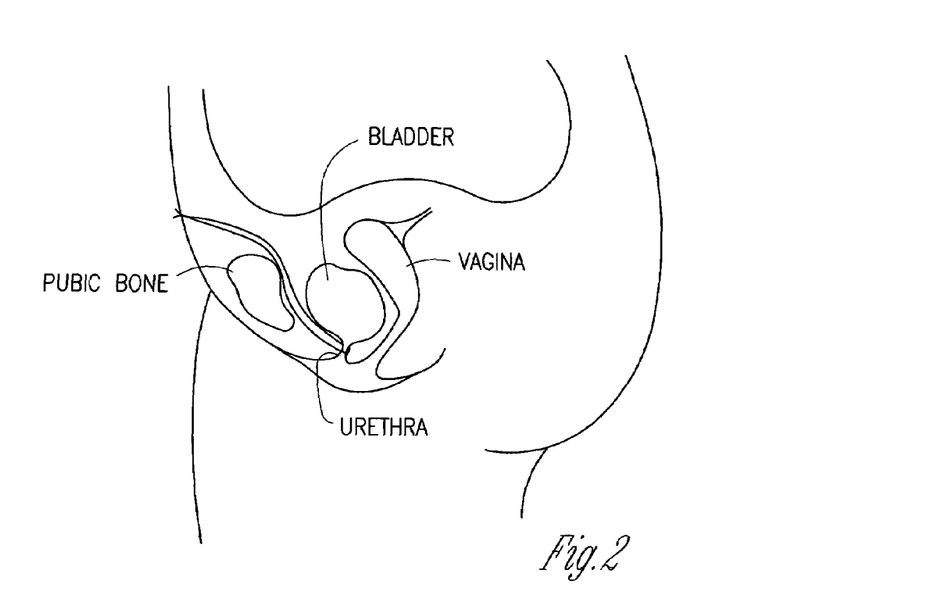
FIG. 2 is a side cross sectional drawing of the female anatomy demonstrating a sling to lift and support the bladder with respect to the pubic bone and to diminish the curvature of the urethra and the bladder neck.

FIG. 2 is a side cross sectional drawing of the female anatomy demonstrating a sling to lift and support the bladder and to diminish the curvature of the urethra and the bladder neck. The bladder is lifted in FIG. 2, as compared to the bladder position in FIG. 1. The urethra near the bladder neck is also supported by the sling and the tissue near the vagina is no longer compressed by the bladder. Attachment of the sling may be made using bone anchoring or suturing to the pubic bone, by attachment to strong ligaments of the female anatomy, such as the Cooper's ligaments, or by attachment to the rectus abdominous muscle. A variety of attachment apparatus and methods are provided in the present description.

Figure 3:
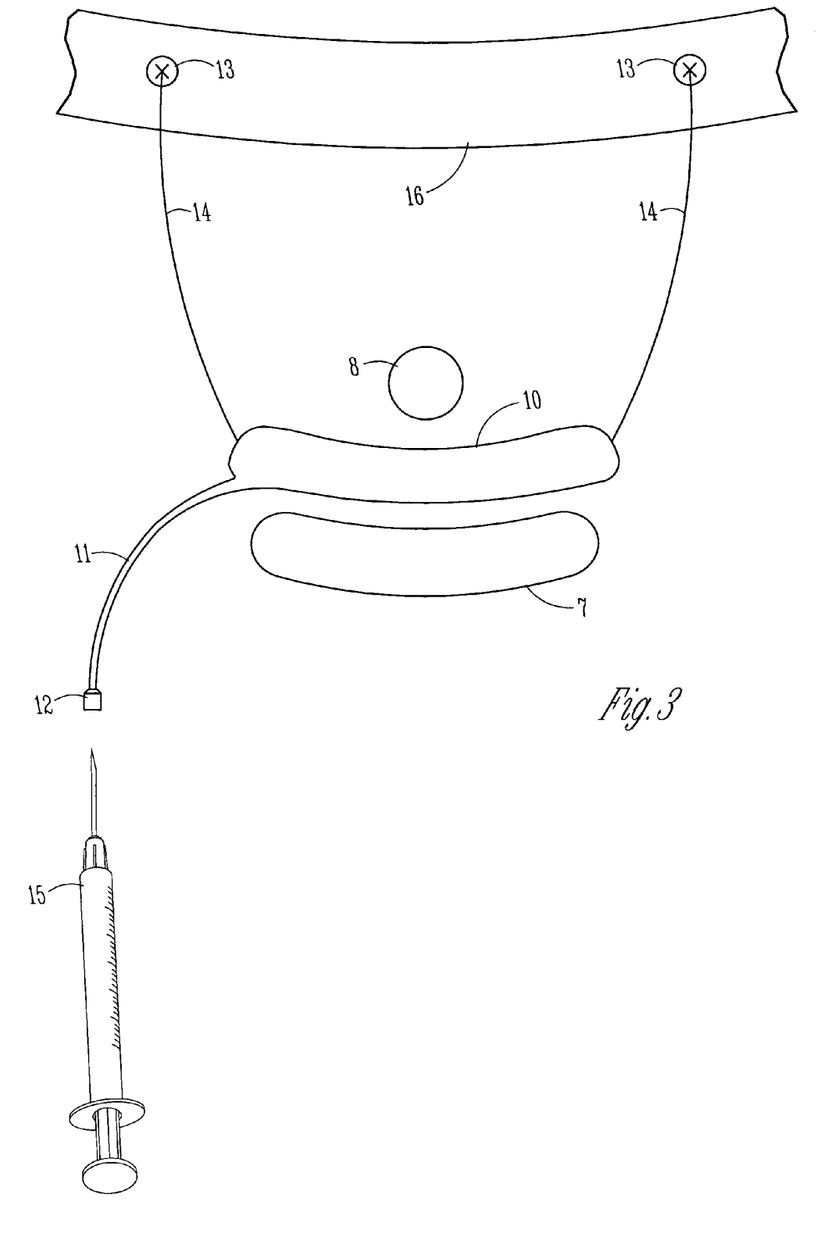
FIG. 3 shows a top cross sectional drawing of the female anatomy from a view where the urethra is normal to the plane of the drawing and showing a cross section of an adjustable sling with an expandable element according to one embodiment of the present system.

FIG. 3 shows a top cross sectional drawing of the female anatomy from a view where the urethra 8 is normal to the plane of the drawing and showing a cross section of an adjustable sling with an expandable element 10 according to one embodiment of the present system. In this embodiment the expandable element 10 is supported by the attachment straps 14 and is positioned between the vagina 7 and the urethra 8 in the region of the bladder neck. Tightening the attachment straps 14 provides a support of the urethra 8 and bladder neck due to forces on the attachment straps 14 and the expandable element 10. The position of the urethra 8 with respect to the pubic bone is adjusted during surgery by controlling the tension on the attachment straps 14, which are connected to the anchors 13, in this embodiment.

The expandable element 10 is made of any biocompatible material which is suitable for implantation and has the requisite mechanical properties for strength, elasticity, and durability. Some suitable materials include silicone and polyurethane. The element is connected to a conduit 11 which terminates in a port, such as a septum 12. The septum 12 is made of a self sealing material which serves as a port for a source of flowable material for adjusting the size of the expandable element and which self seals upon removal of the source of flowable material. The self-sealing material is silicone in one embodiment, however, other materials may be used without departing from the present system. In some embodiments, the flowable material used is a saline solution. Other flowable materials are used in different embodiments, including, but not limited to x-ray contrast media, and/or hydrophilic particle suspensions. Combinations of flowable materials may be used in certain embodiments.

Fluid communication between the septum 12, conduit 11, and expandable element 10 is such that the expandable element may be expanded by adding a flowable material using a source accessing the port (septum 12) or contracted by withdrawing flowable material from the source accessing the port (septum 12). In one embodiment, this adding or withdrawing is an adjustment to the size of the expandable element which is performed postoperatively. In one embodiment this is performed using a syringe 15 containing a flowable material.

Adjustment of the expandable element is facilitated by positioning the septum under the skin and in a region convenient for access by a syringe, such as the labia majora or mons pubis. Other locations and methods for positioning may be used without departing from the present teachings. Thus, conduit 11 is long enough for positioning the septum in a desirable location and tunneling through the tissue back towards the anterior surface of the pubis. This provides a system in which size of the expandable element is adjustable after the implantation of the device. Therefore, the urethra 8 may be displaced in either direction by adding or subtracting flowable material to the expandable element through the septum after surgery. This postoperative adjustment may be made by locating the septum near its expected location and using the syringe 15 to add or withdraw flowable material, adjusting the position of the urethra 8 and the coaptation of the urethra 8 near the bladder neck.

Although FIG. 3 shows anchoring to the pubic bone 16, other embodiments employ other anchoring points, such as the Cooper's ligaments. The straps 14 are anchored to the pubic bone 16 using bone anchors, sutures, or glue. Other attachments may be used without departing from the present system. In one embodiment, the attachment straps are made of nylon. In other embodiments, stainless steel or polypropylene are used. Attachment of the straps 14 to the expandable element is accomplished by use of surgical needles. Alternatively, the expandable element is integrated into the straps 14, where in one embodiment the straps 14 shown on either side of the expandable element form a single continuous strap on which the expandable element, or elements, is positioned/secured.

The expandable element changes in sizes when flowable material is added or withdrawn. In one embodiment, the expandable element varies in sizes between approximately 8-15 mm in thickness. Other ranges may be used without departing from the present system. The expandable element may change in volume in various ranges. In one embodiment a range of 2-20 cc's is used. Other ranges may be employed without departing from the present system.

Figure 4:
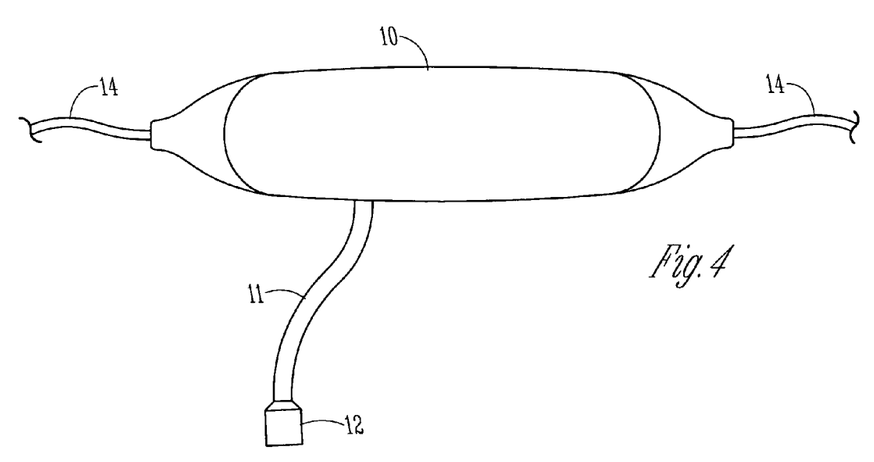
FIG. 4 shows a top view of the adjustable sling according to the one embodiment shown in FIG. 3.

FIG. 4 shows a top view of the adjustable sling according to the one embodiment shown in FIG. 3. The figure is not necessarily drawn to scale and the size of the expandable element and straps may vary without departing from the present invention.

Figure 5:
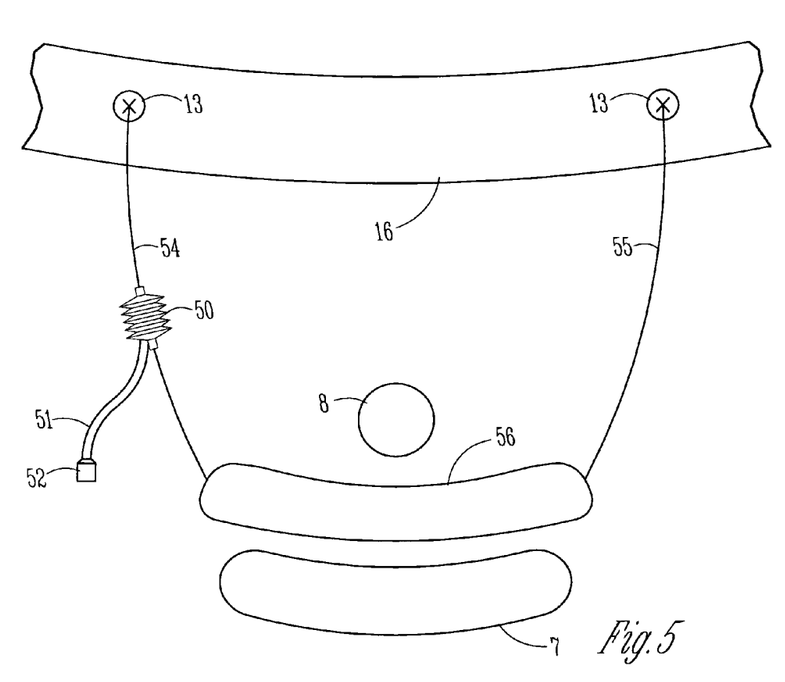
FIG. 5 shows a top cross sectional drawing of the female anatomy from a view where the urethra is normal to the plane of the drawing and showing a cross section of an adjustable sling according to one embodiment of the present system.

FIG. 5 shows a top cross sectional drawing of the female anatomy from a view where the urethra is normal to the plane of the drawing and showing a cross section of an adjustable sling according to one embodiment of the present system. In this embodiment, strap 54 is modified to include an adjustable element 50 for adjusting the tension in strap 54 and for changing the displacement of the urethra 8, accordingly. Adjustment of element 50 is performed by adding or subtracting flowable material to element 50 using septum 52 in fluid communication with conduit 51.

In one embodiment element 50 is a bellows with a length that is a function of the flowable material added to the bellows. This provides an adjustment of the lift or support of the bladder near the bladder neck in this embodiment.

It is understood that element 50 may be located on different portions of strap 54 in some embodiments. Other embodiments include the use of element 50 on both strap 54 and strap 55. Another embodiment includes the use of multiple elements 50 to provide additional displacement of urethra 8. In some embodiments, sling 56 is not adjustable. In some embodiments, sling 56 is a conventional sling. In some embodiments, sling 56 is adjustable, including any of the embodiments provided in this specification.

Figure 6:
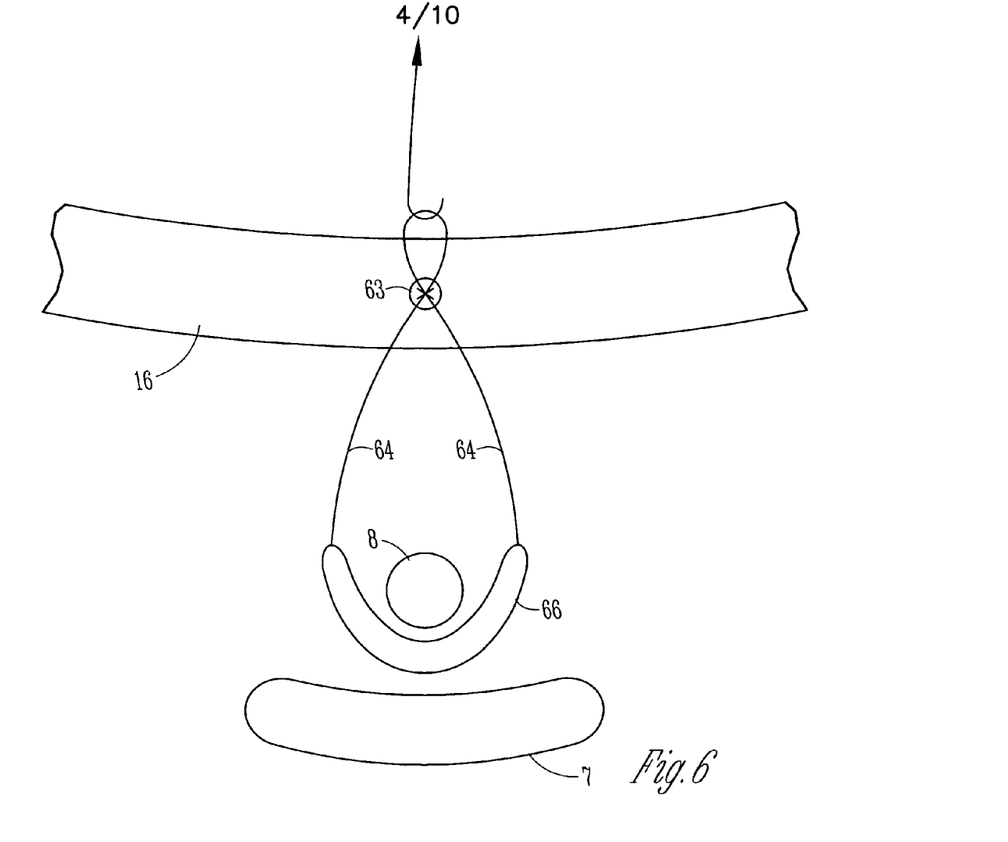
FIG. 6 shows a top cross sectional drawing of the female anatomy from a view where the urethra is normal to the plane of the drawing and showing a cross section of an adjustable sling according to one embodiment of the present system.

FIG. 6 shows a top cross sectional drawing of the female anatomy from a view where the urethra is normal to the plane of the drawing and showing a cross section of an adjustable sling according to one embodiment of the present system. In this embodiment, an adjustable anchor 63 is incorporated into a single connection point for straps 64. Sling 66 is connected to the straps 64. The tension on sling 66 is adjustable by changing settings at adjustable anchor 63.

Figure 7:
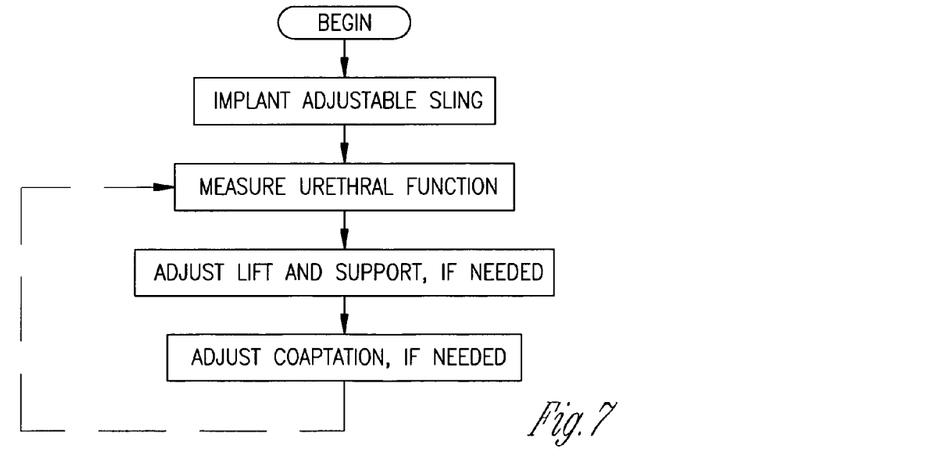
FIG. 7 is a flow chart showing one example of a procedure for adjusting one embodiment of the adjustable sling.

FIG. 7 shows one embodiment of a process for adjusting both the lift and support of the bladder/bladder neck and the coaptation of the urethra near the bladder neck. In this embodiment, an adjustable mount for the sling and an expandable element are used to provide adjustment of the lift and support and to provide adjustment of the coaptation of the urethra. The adjustable sling is implanted and the lift and support provided by the sling is initially adjusted. The expandable element is only partially filled. After implantation, the urethral function is measured. The lift and support of the sling is adjusted first and then the coaptation is adjusted by filling or withdrawing flowable material from the expandable element.

FIG. 8-11 are shown to demonstrate different adjustable slings and are not necessarily drawn to scale. The following discussion is applicable to the remaining figures in different embodiments and is not limited to FIG. 8.

Figure 8A:
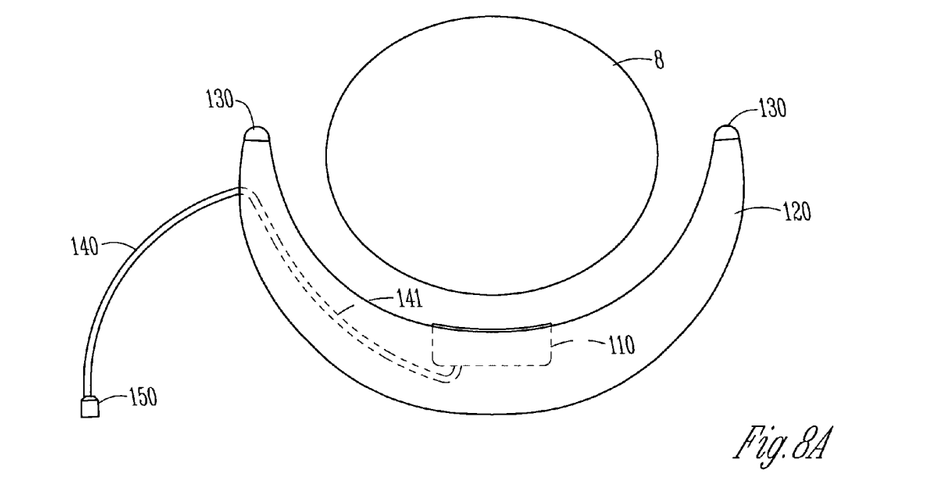
FIG. 8A is a cross sectional view of an adjustable sling according to one embodiment of the present system to demonstrate an uninflated state.

One embodiment of an adjustable sling is demonstrated in FIG. 8. FIG. 8A is a cross sectional view of an adjustable sling according to one embodiment of the present system to demonstrate an uninflated state. In this embodiment, sling cup 120 contains an integrated conduit portion 141 which provides an interface for fluid communication between balloon 110 and conduit 140 which terminates in port 150. In some embodiments, port 150 is a self sealing septum. Attachment tabs 130 are connected to straps (not shown) by suture in one embodiment. In one embodiment, tabs 130 contain a perforation so that straps may be tied to each tab 130. The sling is secured using any of the connection systems and methods described in this specification, including all of the adjustable apparatus and methods taught herein.

Figure 8B:
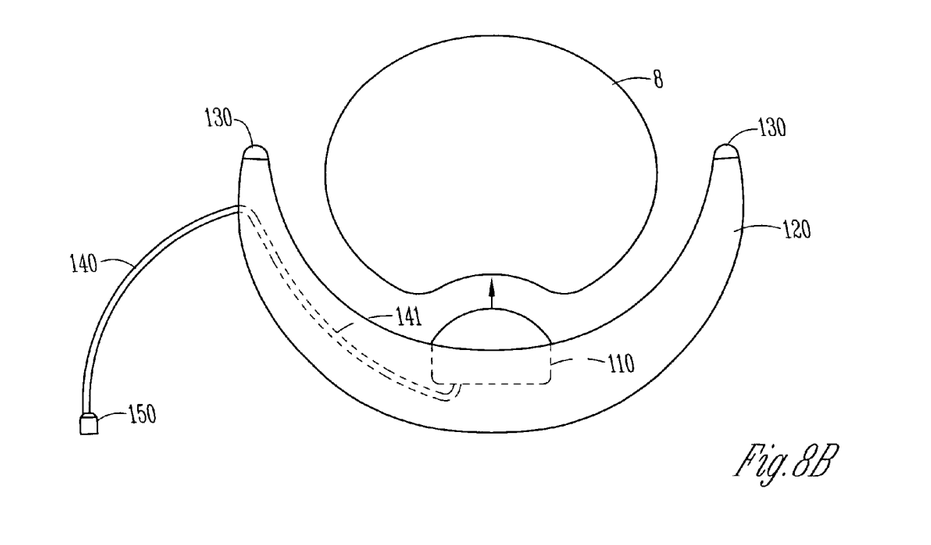
FIG. 8B is a cross sectional view of the adjustable sling of FIG. 8A demonstrating one inflated state.
Figure 8C:
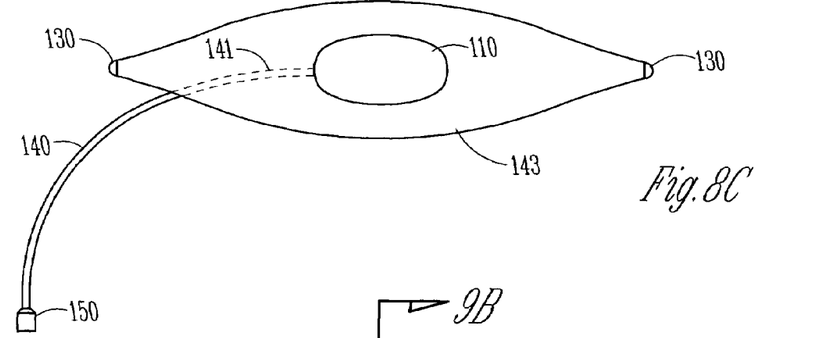
FIG. 8C is a top view of the adjustable sling of FIG. 8A according to one embodiment of the present system.

When properly tensioned, the sling cup 120 provides support and lift to the bladder neck distributed across face 143 (shown in FIG. 8C). Coaptation of the urethra near the bladder neck is further adjustable using balloon 110 which is inflated to provide force on urethra 8 to assist in providing adequate coaptation for alleviating type III urinary stress incontinence. In one embodiment port 150 is located at a position which is easy to access by a source of flowable material, such as a syringe. Using this embodiment, urethral coaptation is substantially independently adjustable of the lift and support of the bladder by cup 120. FIG. 8B is a cross sectional view of the adjustable sling of FIG. 8A demonstrating one inflated state. In one embodiment, the coaptation of urethra 8 is adjustable after the implantation of device to provide enhanced coaptation without requiring another surgery.

The drawing of the balloon 110 is not necessarily to scale, and the location, size, and maximum size of the balloon 110 may differ without departing from the present system. For example, different shaped balloons may be employed and other variations may be used, such as balloons which expand to a predetermined shape. Several embodiments are possible without departing from the present teachings.

Cup 120 is made of any biocompatible material. In one embodiment cup 120 is flexible for ease of implantation. Implantation of such device may be performed through a vaginal incision method. In another embodiment, cup 120 is semi-rigid to accommodate the integrated conduit portion 141.

FIG. 8C is a top view of the adjustable sling of FIG. 8A according to one embodiment of the present system. The size, shape and position of balloon 110 with respect to surface 143 may change without departing from the present system.

Figure 9A:
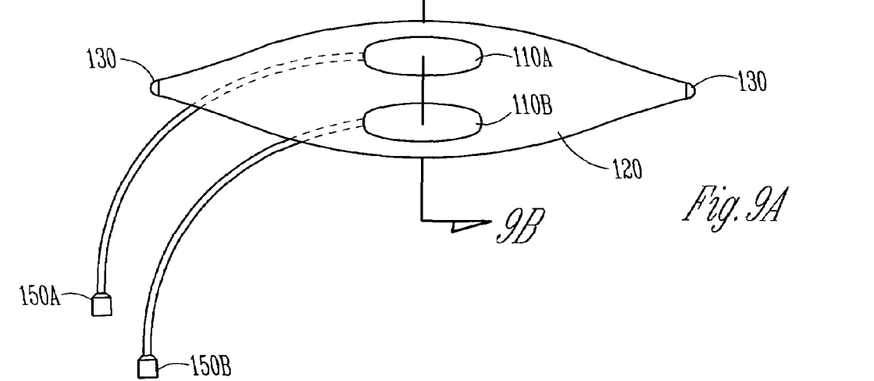
FIG. 9A is a top view of the adjustable sling according to one embodiment of the present system.
Figure 12:
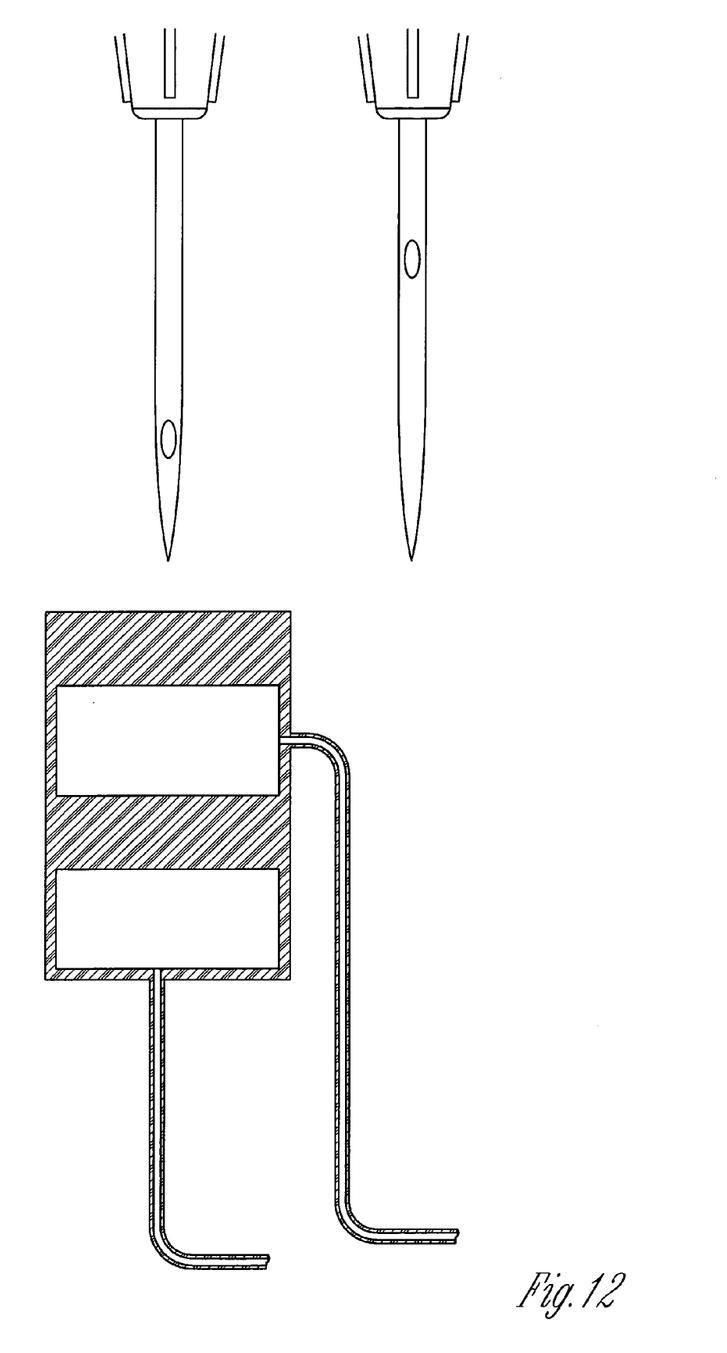
FIG. 12 is a diagram of a one embodiment of a multiple port system.

FIG. 9A is a top view of the adjustable sling according to one embodiment of the present system. In this embodiment, multiple balloons 110a and 110b are used to better control the coaptivity of the urethral portion near the bladder. Multiple ports 150a and 150b are also used to independently control the expansion of each balloon. In one embodiment a septum having dual ports is used to provide fluid communication to the plurality of balloons, as is shown in FIG. 12.

Figure 9B:
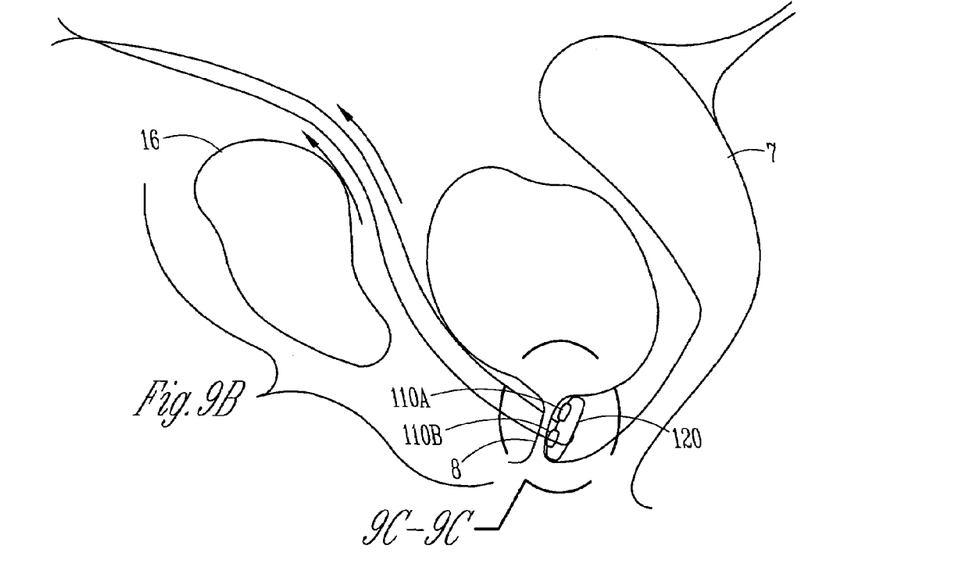
FIG. 9B and FIG. 9C show a side cross sectional drawing of the female anatomy demonstrating the adjustable sling of FIG. 9A to lift and support the bladder with respect to the pubic bone and to diminish the curvature of the urethra at the bladder neck, the adjustable sling also providing adjustable urethral coaptation.
Figure 9C:
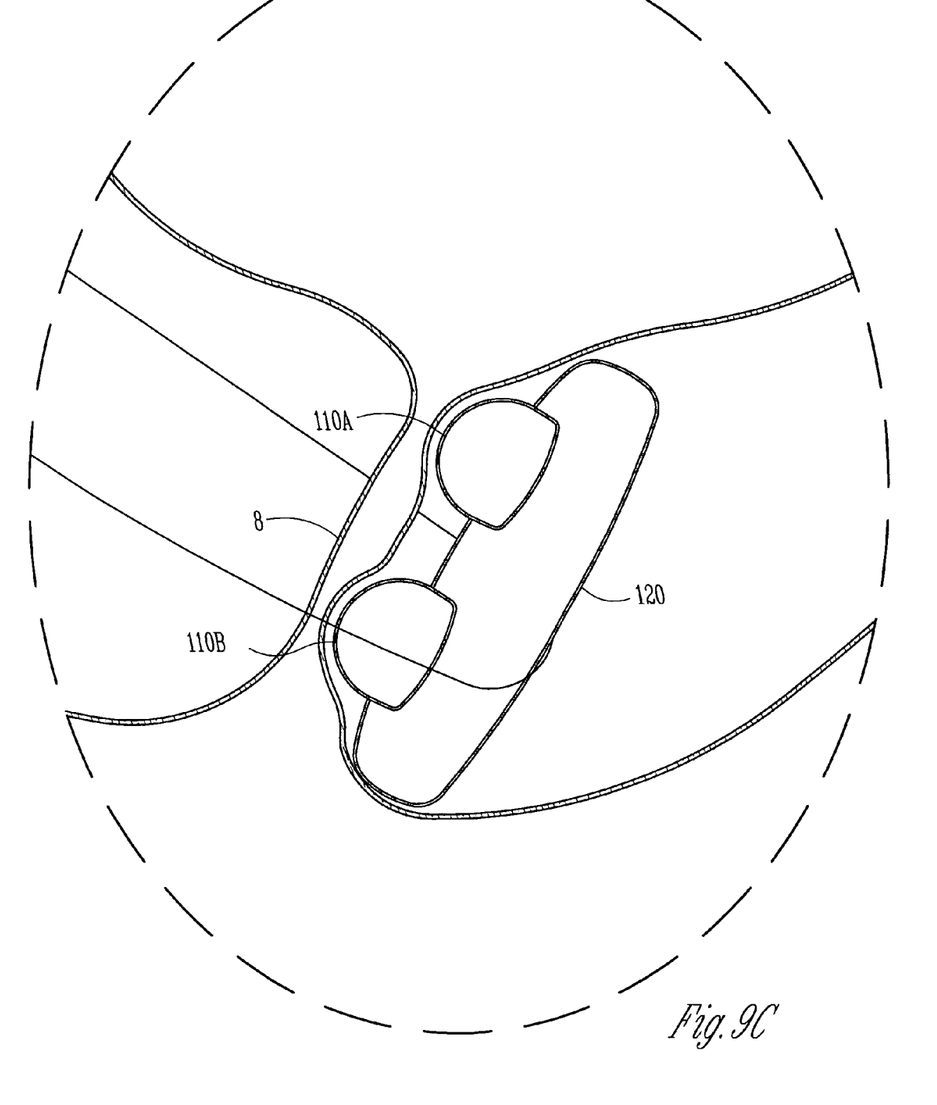

FIG. 9B and FIG. 9C show a side cross sectional drawing of the female anatomy demonstrating the adjustable sling of FIG. 9A to lift and support the bladder with respect to the pubic bone and to diminish the curvature of the urethra at the bladder neck, the adjustable sling also providing adjustable urethral coaptation. This figure shows the mechanical forces on the bladder neck portion of the urethra due to the sling straps and due to the effect of the balloons 110a and 110b on the urethra. In one embodiment, the inflation of the balloons is independently adjustable to provide the proper amount of coaptation.

Figure 10A:
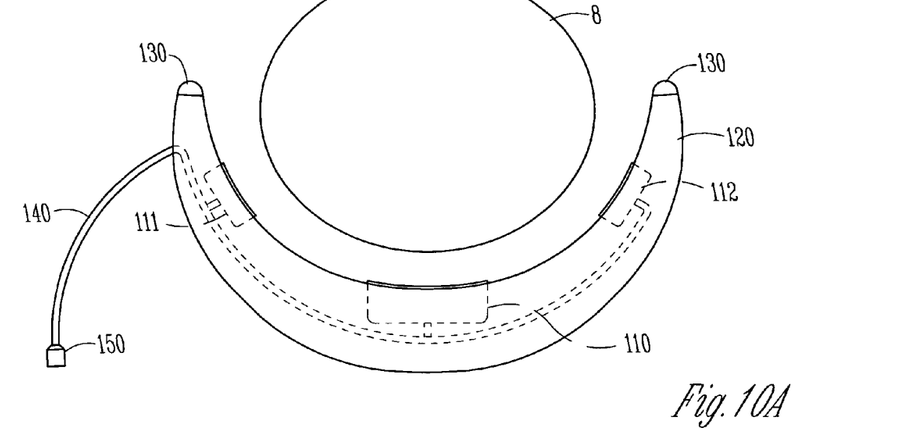
FIG. 10A is a cross sectional view of an adjustable sling according to one embodiment of the present system to demonstrate an uninflated state.

FIG. 10A is a cross sectional view of an adjustable sling according to one embodiment of the present system to demonstrate an uninflated state. In this embodiment all of the balloons are connected to the same conduit, however, other connections may be made without departing from the present system. The additional balloons 111 and 112 provide additional coaptation control by applying force from a plurality of directions. In one embodiment, balloons 111 and 112 are connected to a first common conduit and a first port, and balloon 110 is connected to a separate, second conduit and a separate, second port. This allows balloons 111 and 112 to fill evenly and independently of balloon 110.

Figure 10B:
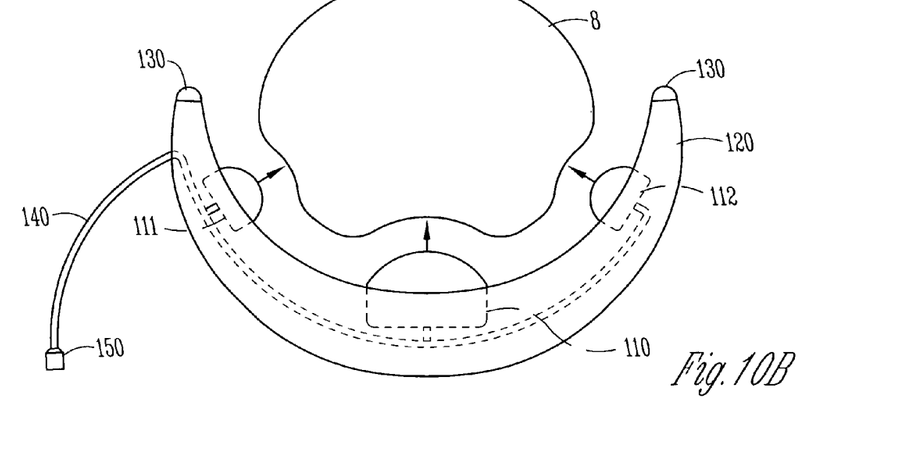
FIG. 10B is a cross sectional view of the adjustable sling of FIG. 10A demonstrating one inflated state.

FIG. 10B is a cross sectional view of the adjustable sling of FIG. 10A demonstrating one inflated state. Sling cup 120 has a surface 143 (FIG. 10C) which provides the lift and support of the bladder when properly connected to straps (not shown) at tabs 130. The additional coaptive forces on the urethra 8 due to the inflation are shown with arrows.

Figure 10C:
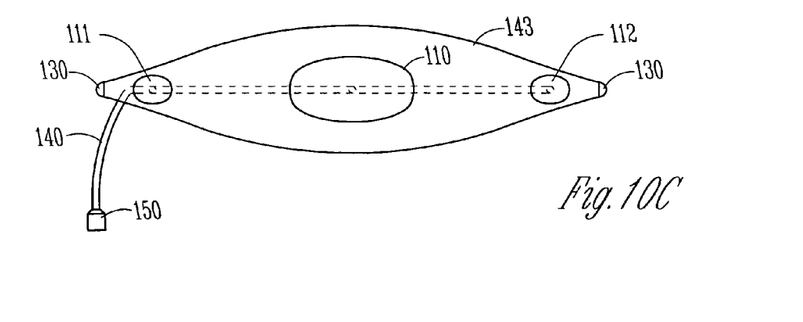
FIG. 10C is a top view of the adjustable sling of FIG. 10A according to one embodiment of the present system.

FIG. 10C is a top view of the adjustable sling of FIG. 10A according to one embodiment of the present system. The shapes, placement, and sizes of the balloons may change without departing from the present system.

Figure 11A:
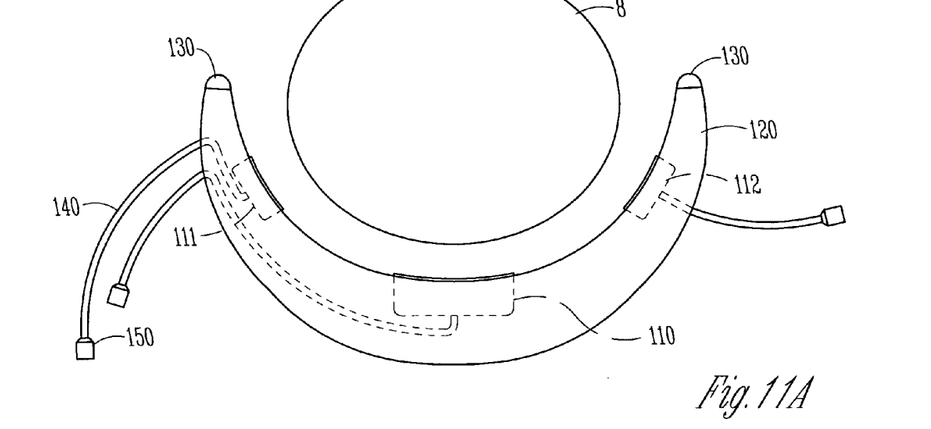
FIG. 11A is a cross sectional view of an adjustable sling according to one embodiment of the present system to demonstrate an uninflated state.

FIG. 11A is a cross sectional view of an adjustable sling according to one embodiment of the present system to demonstrate an uninflated state. In this embodiment, a plurality of ports and independent conduits are used to independently fill each balloon. However, it is noted that it may be advantageous in other embodiments to connect conduits to balloons 111 and 112 to provide even filling. Furthermore, in some embodiments a septum having a plurality of ports may be used to have a common position where each balloon may be filled, as is shown in FIG. 12. Additional ports may be added to the structure of FIG. 12.

Figure 11B:
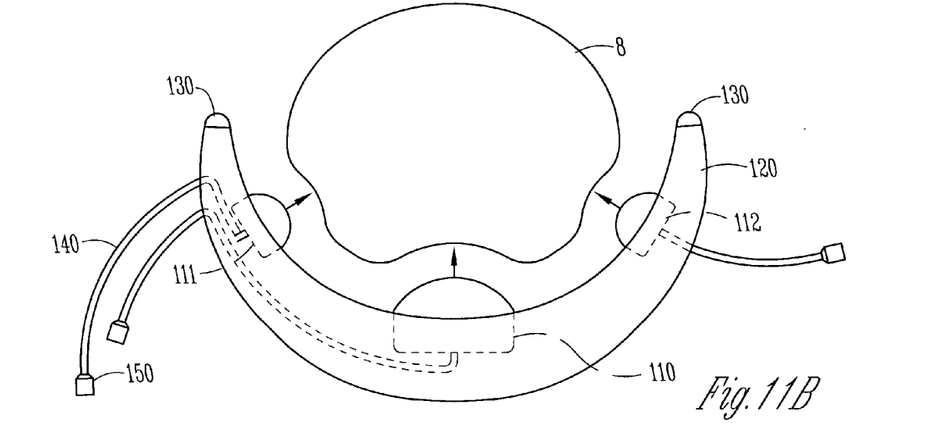
FIG. 11B is a cross sectional view of the adjustable sling of FIG. 11A demonstrating one inflated state.

FIG. 11B is a cross sectional view of the adjustable sling of FIG. 11A demonstrating one inflated state. Sling cup 120 has a surface 143 (FIG. 10C) which provides the lift and support of the bladder when properly connected to straps (not shown) at tabs 130. The additional coaptive forces on the urethra 8 due to the inflation are shown with arrows.

Figure 11C:
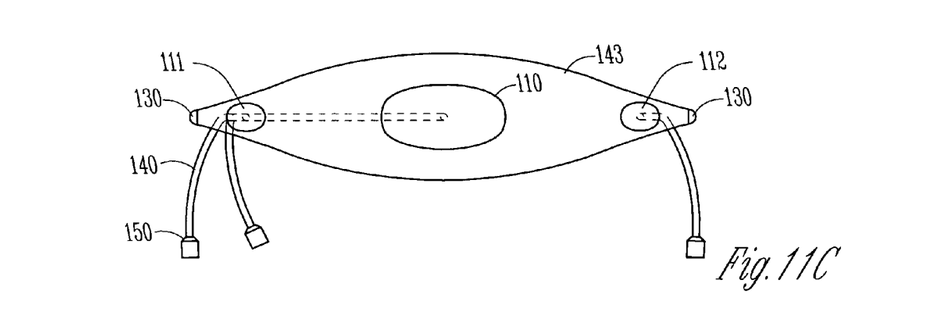
FIG. 11C is a top view of the adjustable sling of FIG. 11A according to one embodiment of the present system.

FIG. 11C is a top view of the adjustable sling of FIG. 11A according to one embodiment of the present system. The shapes, placement, and sizes of the balloons may change without departing from the present system.

CONCLUSION

Upon reading and understanding the present description, those skilled in the art would recognize that minor variations in the apparatus, processes, and applications described herein may exist without departing from the claimed invention and its equivalents. The embodiments described herein are intended to demonstrate the present invention, and are not intended in an exclusive or limited sense. For example, a change in the positioning of adjustable elements, filling fluids, shapes, conduit layout and connectivity, and filling systems may occur without departing from the present system. Furthermore, the shapes, placement, and sizes of the balloons may change without departing from the present system.

What is claimed is:

1. An implantable device, comprising:
   an anchoring system;
   one or more bands including one or more hydraulic bellows, the one or more bands connected to the anchoring system; and
   an implantable sling cup, connected to the one or more bands and including an expandable element,
   wherein the expandable element is connected to a self sealing port via a conduit and is adjustable by adding or withdrawing flowable material from an external source to affect expansion of the expandable element.

2. The implantable device of claim 1, wherein the expandable element is adjustable by connection to a source of flowable material.

3. The implantable device of claim 1, wherein the self sealing port is a septum.

4. The implantable device of claim 1, wherein the hydraulic bellows are connected to a septum.

5. The implantable device of claim 1, wherein the sling cup includes a plurality of expandable elements.

6. The implantable device of claim 5, wherein the plurality of expandable elements are attached to one or more septums.

7. An implantable device for a body having a urethra, comprising:
   a sling having a cup and one or more straps, the one or more straps adapted to be anchored within the body; and
   at least one expandable element integral to the cup to change position of the urethra, and a hydraulic bellows forming an integral portion of the one or more straps.

8. The implantable device of claim 7, wherein the hydraulic bellows are connected to a septum.

9. An implantable device for a body having a urethra, comprising:
   a sling including a cup including a plurality of adjustable elements attached to one or more septums and the sling having one or more straps, the one or more straps adapted to be anchored within the body;
   at least one expandable element integral to the cup to change position of the urethra; and
   hydraulic bellows forming an integral portion of the one or more straps.

10. The implantable device of claim 9, wherein the hydraulic bellows are connected to a septum.

11. An implantable device for a body having a urethra, comprising:
    a sling having a cup and one or more straps, the one or more straps adapted to be anchored within the body; and
    a plurality of expandable elements integral to the cup to change position of the urethra, the plurality of adjustable elements attached to one or more septums.

12. An implantable, adjustable sling for a body, comprising:
    an implantable sling cup connected to a first strap and a second strap, the first strap and the second strap adapted to be anchored within the body; and at least one adjustable element forming an integral portion of the first strap;

wherein the sling cup comprises an expandable element connected to a conduit including a self-sealing port, the expandable element adapted to be expanded by adding flowable material or contracted by withdrawal of flowable material.

13. An implantable, adjustable sling for a body, comprising:

an implantable sling cup connected to a first strap and a second strap, the first strap and the second strap adapted to be anchored within the body; and at least one adjustable element forming an integral portion of the first strap;

wherein the sling cup comprises a plurality of balloons connected to conduits including self-sealing ports, the plurality of balloons adapted to be expanded by adding flowable material or contracted by withdrawal of flowable material.

14. An implantable, adjustable sling for a body, comprising:

an implantable sling cup connected to a first strap and a second strap, the first strap and the second strap adapted to be anchored within the body; and at least one adjustable element forming an integral portion of the first strap;

wherein the sling cup comprises a plurality of balloons connected to one or more conduits including one or more self-sealing ports, the plurality of balloons adapted to be expanded by adding flowable material or contracted by withdrawal of flowable material.

15. The implantable, adjustable sling of claim 14, wherein each balloon of the plurality of balloons is connected to a single conduit.

16. The implantable, adjustable sling of claim 14, wherein each balloon of the plurality of balloons is connected to an independent conduit.

17. An implantable, adjustable sling for a body, comprising:

an implantable sling cup connected to a first strap and a second strap, the first strap and the second strap adapted to be anchored within the body; and at least one adjustable element forming an integral portion of the first strap;

wherein the first strap comprises a plurality of adjustable elements.

18. An implantable, adjustable sling for a body, comprising:

an implantable sling cup connected to a first strap and a second strap, the first strap and the second strap adapted to be anchored within the body; and at least one adjustable element forming an integral portion of the first strap, the at least one adjustable element adapted to be adjusted by adding or subtracting flowable material;

wherein the second strap comprises another adjustable element.

19. An implantable, adjustable sling for a body, comprising:

an implantable sling cup connected to a first strap and a second strap, the first strap and the second strap adapted to be anchored within the body; and at least one adjustable element forming an integral portion of the first strap;

wherein the at least one adjustable element includes a hydraulic bellows.

20. The implantable device of claim 19, wherein the hydraulic bellows are connected to a septum.

21. An implantable device, comprising:

an implantable sling cup comprising a plurality of balloons connected to one or more conduits, each conduit including a port, the plurality of balloons adapted to be expanded by adding flowable material or contracted by withdrawal of flowable material.

22. The implantable device according to claim 21, wherein each balloon of the plurality of balloons is connected to a single conduit.

23. The implantable device according to claim 21, wherein each balloon of the plurality of balloons is connected to an independent conduit.

24. The implantable device according to claim 21, further comprising a first strap and a second strap.

25. The implantable device according to claim 21, wherein at least one port includes a self sealing port.

26. The implantable device according to claim 21, wherein at least one port includes a septum.

27. The implantable device according to claim 21, further comprising attachment tabs.

* * * * *